United States Patent
Kameshima et al.

(10) Patent No.: US 8,907,294 B2
(45) Date of Patent: Dec. 9, 2014

(54) IMAGE PICKUP APPARATUS, IMAGE PICKUP SYSTEM, METHOD FOR CONTROLLING IMAGE PICKUP APPARATUS, METHOD FOR CONTROLLING IMAGE PICKUP SYSTEM, AND PROGRAMS

(75) Inventors: Toshio Kameshima, Kumagaya (JP); Tadao Endo, Honjo (JP); Tomoyuki Yagi, Honjo (JP); Katsuro Takenaka, Honjo (JP); Keigo Yokoyama, Honjo (JP); Sho Sato, Kumagaya (JP)

(73) Assignee: Canon Kabushiki Kaisha, Tokyo (JP)

( * ) Notice: Subject to any disclaimer, the term of this patent is extended or adjusted under 35 U.S.C. 154(b) by 316 days.

(21) Appl. No.: 13/502,509

(22) PCT Filed: Jun. 10, 2010

(86) PCT No.: PCT/JP2010/005982
§ 371 (c)(1),
(2), (4) Date: Apr. 17, 2012

(87) PCT Pub. No.: WO2011/052137
PCT Pub. Date: May 5, 2011

(65) Prior Publication Data
US 2012/0217413 A1    Aug. 30, 2012

(30) Foreign Application Priority Data
Oct. 26, 2009    (JP) .................................. 2009-245805

(51) Int. Cl.
| | |
|---|---|
| G01J 1/42 | (2006.01) |
| A61B 6/00 | (2006.01) |
| H04N 5/378 | (2011.01) |
| H04N 5/374 | (2011.01) |
| H04N 5/3745 | (2011.01) |
| H04N 5/32 | (2006.01) |
| G01T 7/00 | (2006.01) |

(52) U.S. Cl.
CPC ................. G01T 7/005 (2013.01); A61B 6/585 (2013.01); H04N 5/378 (2013.01); A61B 6/4233 (2013.01); A61B 6/4441 (2013.01); H04N 5/3742 (2013.01); H04N 5/37455 (2013.01); H04N 5/32 (2013.01)
USPC ....................................................... 250/394

(58) Field of Classification Search
CPC ............................ H04N 5/32; H04N 5/37455
USPC ................................ 250/394, 370.01–370.15
See application file for complete search history.

(56) References Cited

U.S. PATENT DOCUMENTS

2010/0104071 A1* 4/2010 Nys ................................ 378/98

FOREIGN PATENT DOCUMENTS

| JP | 59060383 A | 4/1984 |
|---|---|---|
| JP | 4144423 A | 5/1992 |

(Continued)

*Primary Examiner* — Kiho Kim
(74) *Attorney, Agent, or Firm* — Canon USA Inc. IP Division

(57) ABSTRACT

An image pickup apparatus includes a detector having pixels divided into first and second pixel groups, a signal processor including a reading circuit unit including first and second reading circuits, an A/D conversion unit including first and second A/D converters, a digital data processing circuit, and a controller. The controller instructs the signal processor to perform a signal processing operation several times of adding direct current potentials to analog electric signals of pixels from the reading circuit unit, supplying the signals to the A/D conversion unit, and outputting digital data to the digital data processing circuit while the direct current potentials are changed, and an average processing operation of averaging the digital data for the pixels using the digital data processing circuit.

14 Claims, 9 Drawing Sheets

(56) References Cited

FOREIGN PATENT DOCUMENTS

| | | | |
|---|---|---|---|
| JP | 6045933 A | 2/1994 |
| JP | 6090173 A | 3/1994 |
| JP | 2005210396 A | 8/2005 |
| JP | 2005210480 A | 8/2005 |
| JP | 2006025189 A | 1/2006 |

\* cited by examiner

IMAGE PICKUP APPARATUS, IMAGE PICKUP SYSTEM, METHOD FOR CONTROLLING IMAGE PICKUP APPARATUS, METHOD FOR CONTROLLING IMAGE PICKUP SYSTEM, AND PROGRAMS

TECHNICAL FIELD

The present invention relates to image pickup apparatuses, image pickup systems, methods for controlling the image pickup apparatuses and image pickup systems, and programs. Particularly, the present invention relates to a radiation image pickup apparatus and a radiation image pickup system suitably used for still-image shooting such as general shooting in medical diagnosis and moving-image shooting such as fluorography, methods for controlling them, and programs. Note that, in the present invention, radiation includes, in addition to alpha-rays, beta-rays, and gamma-rays which are generated by particles (including photons) emitted due to radioactive decay, beams which have energy equal to or larger than that of the alpha-rays, the beta-rays, and the gamma-rays and which include x-rays, particle beams, and cosmic rays.

BACKGROUND ART

In recent years, as an image pickup apparatus used for medial image diagnosis and nondestructive inspection, a radiation image pickup apparatus utilizing a flat panel detector (hereinafter referred to as an "FPD") formed of semiconductor material has been put into practical use. Such a radiation image pickup apparatus is used as a digital image pickup apparatus for still-image shooting such as general shooting and moving-image shooting such as fluorography in medical image diagnosis.

Such a radiation image pickup apparatus includes the detector described above, a driving circuit which drives the detector, a reading circuit which reads an analog electric signal from the detector, and an A/D converter which converts the analog electric signal into a digital signal. The A/D converter outputs a digital image signal obtained at a time of shooting and an image signal used for correction. When an image signal is to be output from the image pickup apparatus within a short period of time, the image pickup apparatus includes a plurality of A/D converters.

However, the A/D converter may generate nonlinearity which is not ideal linearity characteristic as a conversion characteristic (A/D conversion characteristic) between an input analog electric signal and an output digital signal. In particular, if an image pickup apparatus has a plurality of A/D converters, nonlinearities of the A/D converters differ from one another and an image generated from digital signals may cause a feeling of strangeness due to unevenness of the image, for example. When such a feeling of strangeness is generated due to the unevenness or the like, it is preferable that the nonlinearity is suppressed or an adverse effect caused by the nonlinearity is corrected.

Patent Literature 1 discloses an A/D conversion circuit which stores a reference signal which is synchronized with a signal output from an A/D conversion unit as address data in a portion corresponding to an address specified by the signal output from the A/D conversion unit and which corrects the signal output from the A/D conversion unit in accordance with the reference signal. Use of this A/D conversion circuit enables reduction of a feeling of strangeness of an image caused by nonlinearity of the A/D conversion unit and realizes high image quality.

Furthermore, Patent Literature 2 discloses an A/D conversion circuit including a correction unit which corrects signals output from a plurality of A/D conversion units in accordance with one of the signals output from the A/D conversion units. Use of this A/D conversion circuit enables reduction of a feeling of strangeness caused by differences among nonlinearities of the A/D conversion units and realizes high image quality.

CITATION LIST

Patent Literature

PTL 1: Japanese Patent Laid-Open No. 2005-210480
PTL 2: Japanese Patent Laid-Open No. 2005-210396

SUMMARY OF INVENTION

Technical Problem

In Patent Literatures 1 and 2, the feeling of strangeness caused by nonlinearities of the A/D converters is suppressed by correcting digital signals output from the A/D converters as described above. However, there arises a problem in that, when the corrections disclosed in Patent Literatures 1 and 2 are to be performed, a number of circuits are required for correcting the digital signals. Furthermore, a process of obtaining conversion data used to correct the nonlinearities of the A/D converters in advance and a process of performing digital correction every time a digital signal is output are required, and accordingly, a system is complicated.

The present invention provides an image pickup apparatus and an image pickup system which have simple configuration and which are capable of reducing a feeling of strangeness caused by an unevenness of an image due to differences among nonlinearities of a plurality of A/D converters by performing simple processes.

Solution to Problem

The inventor of this application has attained the following embodiments of the present invention after a great deal of consideration.

According to an embodiment of the present invention, there is provided an image pickup apparatus including a detector configured to include a plurality of pixels which are arranged in a matrix, which are used to convert a radial-ray or a light beam into analog electric signals, and which are divided into at least first and second pixel groups, a signal processor configured to include a reading circuit unit which includes a first reading circuit electrically connected to the first pixel group and a second reading circuit electrically connected to the second pixel group and which reads the analog electric signals output from the detector on a row-by-row basis, an A/D conversion unit which includes a first A/D converter electrically connected to the first reading circuit and a second A/D converter electrically connected to the second reading circuit and which converts the analog electric signals output from the reading circuit unit into digital data items and outputs the digital data items, and a digital data processing circuit which processes the digital data items, and a controller configured to control the signal processor. The controller controls the signal processor so that the signal processor performs a signal processing operation several times of adding direct current potentials to analog electric signals of certain pixels output from the reading circuit unit, supplying the resultant signals to the A/D conversion unit, and outputting digital data items to the digital data processing circuit while the direct current potentials are changed, and an average processing operation of averaging the output digital data items corresponding to the certain pixels using the digital data processing circuit.

According to another embodiment of the present invention, there is provided a method for controlling an image pickup apparatus including a detector configured to include a plurality of pixels which are arranged in a matrix, which are used to convert a radial-ray or a light beam into analog electric signals, and which are divided into at least first and second pixel groups, and a signal processor configured to include a reading circuit unit which includes a first reading circuit electrically connected to the first pixel group and a second reading circuit electrically connected to the second pixel group and which reads the analog electric signals output from the detector on a row-by-row basis, an A/D conversion unit which includes a first A/D converter electrically connected to the first reading circuit and a second A/D converter electrically connected to the second reading circuit and which converts the analog electric signals output from the reading circuit unit into digital data items and outputs the digital data items, and a digital data processing circuit which processes the digital data items. The method includes a signal processing operation of adding direct current potentials to analog electric signals of certain pixels output from the reading circuit unit, supplying the resultant signals to the A/D conversion unit, and outputting digital data items to the digital data processing circuit while the direct current potentials are changed which is performed several times, and an average processing operation of averaging the output digital data items corresponding to the certain pixels using the digital data processing circuit.

According to a further embodiment of the present invention, there is provided a program which causes a computer to control an image pickup apparatus including a detector configured to include a plurality of pixels which are arranged in a matrix, which are used to convert a radial-ray or a light beam into analog electric signals, and which are divided into at least first and second pixel groups, and a signal processor configured to include a reading circuit unit which includes a first reading circuit electrically connected to the first pixel group and a second reading circuit electrically connected to the second pixel group and which reads the analog electric signals output from the detector on a row-by-row basis, an A/D conversion unit which includes a first A/D converter electrically connected to the first reading circuit and a second A/D converter electrically connected to the second reading circuit and which converts the analog electric signals output from the reading circuit unit into digital data items and outputs the digital data items, and a digital data processing circuit which processes the digital data items. The program causes the computer to perform control on the image pickup apparatus including the steps of performing an operation of adding direct current potentials to analog electric signals of certain pixels output from the reading circuit unit, supplying the resultant signals to the A/D conversion unit, and outputting digital data items to the digital data processing circuit while the direct current potentials are changed which is performed several times, and averaging the output digital data items corresponding to the certain pixels using the digital data processing circuit.

Advantageous Effects of Invention

Accordingly, an image pickup apparatus and an image pickup system capable of reducing a feeling of strangeness due to unevenness of an image caused by differences among nonlinearities of A/D converters with a simple configuration and a simple process can be provided.

DESCRIPTION OF EMBODIMENT

A preferred embodiment of the present invention will be described hereinafter with reference to the accompanying drawings.

Figure 1:
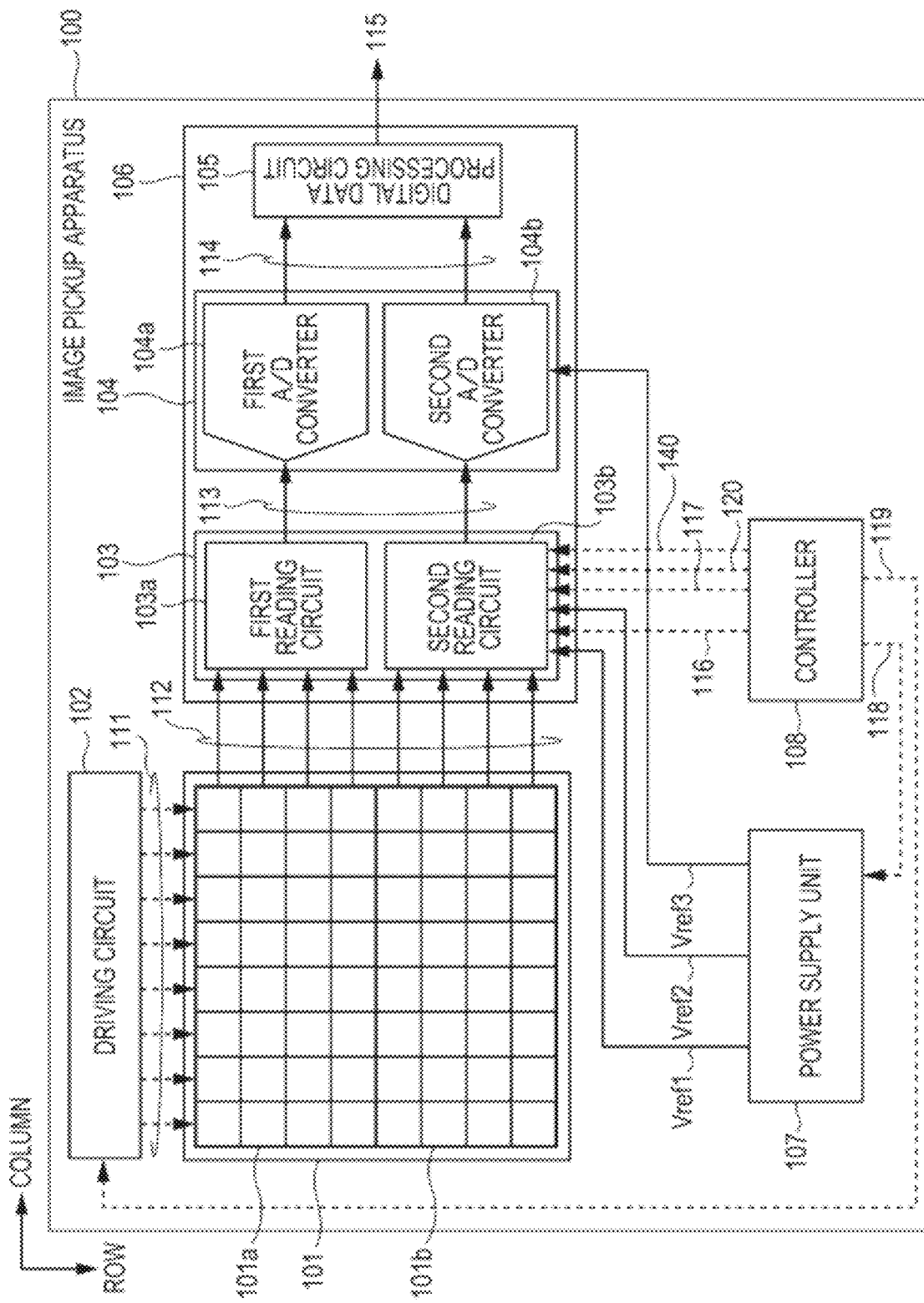
FIG. 1 is a block diagram schematically illustrating an image pickup apparatus according to an embodiment of the present invention.

FIG. 1 is a block diagram schematically illustrating an image pickup apparatus according to an embodiment of the present invention. An image pickup apparatus 100 shown in FIG. 1 includes a detector 101 including a plurality of pixels which are used to convert radial rays or light beams into analog electric signals and which are arranged in a matrix and a driving circuit 102 which drives the detector 101 so that the analog electric signals are output. In this embodiment, for simplicity of description, the detector 101 includes pixels arranged in a matrix of eight rows and eight columns and is divided into a first pixel group 101a and a second pixel group 101b each of which includes four pixel rows. Pixel signals which are analog electric signals output from the pixels included in the first pixel group 101a are read by a first reading circuit 103a which is electrically connected to the first pixel group 101a. Pixel signals 113 which are analog electric signals which have been output from the pixels included in the first reading circuit 103a are converted into digital data 114 by a first A/D converter 104a which is electrically connected to the first reading circuit 103a. Similarly, analog electric signals output from the second pixel group 101b are read by a second reading circuit 103b which is electrically connected to the second pixel group 101b and a second A/D converter 104b which is electrically connected to the second reading circuit 103b and are converted into digital data. The digital data output from the first and second A/D converters 104a and 104b is subjected to a signal process, a digital multiplexing process, an offset correction process, and the like by a digital data processing circuit 105 which will be described hereinafter so as to be output as digital image signals. A signal processor 106 includes a reading circuit unit 103 including the first and second reading circuits 103a and 103b, an A/D conversion unit 104 including the first and second A/D converters 104a and 104b, and the digital data processing circuit 105. Then image pickup apparatus 100 further includes a power supply unit 107 which applies biases to the signal processor 106. The power supply unit 107 applies reference voltages Vref1, Vref2, and Vref3 to the reading circuit unit 103. The image pickup apparatus 100 further includes a controller 108 which controls at least one of the signal processor 106 and the power supply unit 107. The controller 108 supplies a control signal 118 to the power supply unit 107. The controller 108 supplies control signals 116, 117, and 120 to the reading circuit unit 103. Then, the controller 108 supplies a driving control signal 119 to the driving circuit 102. The driving circuit 102 supplies driving signals 111 to the detector 101 in response to the driving control signal 119. Furthermore, the controller 108 supplies an offset control signal 140 which is used to change direct current potentials to be added to signals output from differential amplifiers, which will be described hereinafter, to the reading circuit unit 103.

Figure 2A:
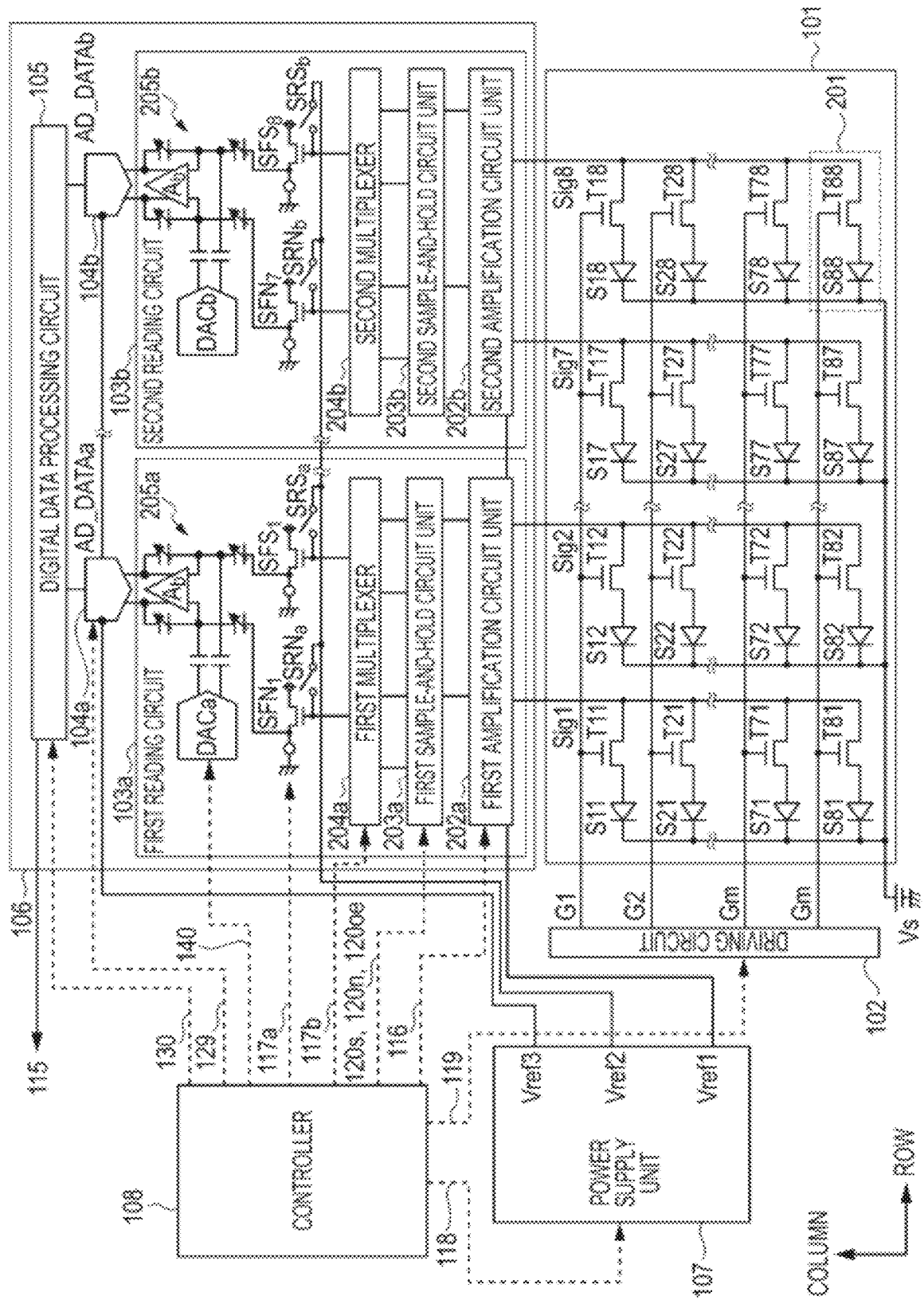
FIG. 2A is a diagram schematically illustrating an image pickup system including a diagram schematically illustrating an equivalent circuit of the image pickup apparatus according to the embodiment of the present invention.

FIG. 2A is a diagram schematically illustrating an image pickup system including a diagram schematically illustrating an equivalent circuit of the image pickup apparatus according to the embodiment of the present invention. Note that components the same as those shown in FIG. 1 are denoted by reference numerals the same as those used in FIG. 1, and therefore, detailed descriptions thereof are omitted. The detector 101 includes a plurality of pixels 201 arranged in a matrix. In FIG. 2A, the 8*8 pixels 201 are arranged in a matrix of eight rows and eight columns. Each of the pixels 201 includes a conversion element S which converts a radial ray or a light beam into a charge and a switching element T which outputs an electric signal corresponding to the charge. As the conversion element S which converts a light beam into a charge, a photoelectric conversion element such as a PIN photodiode mainly including amorphous silicon which is disposed on an insulation substrate such as a glass substrate is suitably used. As the conversion element S which converts a radial ray into a charge, an indirect conversion element which includes a wavelength conversion body which converts a radial ray into a light beam having a wavelength band which can be sensed by the photoelectric conversion element on a radial ray incoming side of the photoelectric conversion element or a direct conversion element which directly converts a radial ray into a charge is suitably used. As the switching element T, a transistor having a control terminal and first and second main terminals is suitably used. When the photoelectric conversion element corresponds to a pixel arranged on the insulation substrate, a thin-film transistor (TFT) is suitably used. One electrode of the conversion element S is electrically connected to one of the first and second main terminals of the switching element T and the other electrode is electrically connected to a bias power supply 106a through a common line. Switching elements T11 to T18, for example, which are included in pixels arranged in the same row have control terminals electrically connected to a driving line G1 of a first row in common and receive a driving signal which is used to control conductive states of the switching elements from the driving circuit 102 through the driving line G on a row-by-row basis. The switching elements in the same column, for example, the switching elements T11 to T81, have second main terminals which are electrically connected to a signal line Sig1 of a first column. While being in conductive states, the switching elements T11 to T81 output electric signals corresponding to charges of corresponding conversion elements to the reading circuit unit 103 through the signal line Sig1. The signal line Sig1 and signal lines Sig2 to Sig8 which are arranged in a column direction transmit electric signals output from the pixels included in the detector 101 to the reading circuit unit 103 in parallel. In this embodiment, the detector 101 is divided into the first pixel group 101a and the second pixel group 101b each of which has four pixel rows. In this embodiment, pixels included in first to fourth rows correspond to first pixels included in the first pixel group 101a and pixels included in fifth to eighth rows correspond to second pixels included in the second pixel group 101b. Analog electric signals output from the first pixel group 101a are read by the first reading circuit 103a included in the reading circuit unit 103 in parallel whereas analog electric signals output from the second pixel group 101b are read by the second reading circuit 103b in parallel.

The first reading circuit 103a includes a first amplification circuit unit 202a which amplifies electric signals output in parallel from the first pixel group 101a and a first sample-and-hold circuit unit 203a which samples and holds electric signals supplied from the first amplification circuit unit 202a. Similarly, the second reading circuit 103b includes a second amplification circuit unit 202b and a second sample-and-hold circuit unit 203b. The first and second reading circuits 103a and 103b include first and second multiplexers 204a and 204b, respectively, which successively output electric signals read in parallel from the first and second sample-and-hold circuit units 203a and 203b as serial image signals. Moreover, the first and second reading circuits 103a and 103b includes first and second differential amplifiers 205a and 205b, respectively, which serve as output buffers which output image signals subjected to impedance conversion. Each of the first and second differential amplifiers 205a and 205b includes a differential amplifier and a variable capacitor. The first and second differential amplifiers 205a and 205b have input terminals connected to D/A converters DACa and DACb, respectively, through capacitors. When the control signal 140 is supplied to the D/A converters DACa and DACb, direct current potentials to be added to signals output from the first and second differential amplifiers 205a and 205b are controlled. A circuit configuration including the D/A converters DACa and DACb and the capacitors corresponds to a direct current potential control circuit. Electric signals output from the pixels are supplied through a signal buffer SFS to the first differential amplifier 205a or the second differential amplifier 205b. Furthermore, noise components are supplied through a noise buffer SFN to the first differential amplifier 205a or the second differential amplifier 205b. The noise components are subtracted from the electric signals output from the pixels which have been input to the first differential amplifier 205a and resultant signals are output to the first A/D converter 104a. Similarly, the noise components are subtracted from the electric signals output from the pixels which have been input to the second differential amplifier 205b and resultant signals are output to the second A/D converter 104b. The power supply unit 107 supplies the reference voltage Vref3 to the first and second A/D converters 104a and 104b. Here, the power supply unit 107 supplies the reference voltage Vref2 to gates of signal buffers SFS of the first and second reading circuits 103a and 103b through reset switches SRS at a predetermined timing. Furthermore, the power supply unit 107 supplies the reference voltage Vref2 to gates of noise buffers SFN of the first and second reading circuits 103a and 103b through reset switches SRN at a predetermined timing. That is, the reset switches SRS and SRN supply the reference voltage Vref2 to the gates of the buffers SFS and SFN at a predetermined timing whereby signals input to the differential amplifiers 205a and 205b are reset at a predetermined timing.

The controller 108 supplies a control signal 116 to the first and second amplification circuit units 202a and 202b. Furthermore, the controller 108 supplies a control signal 117a to the reset switches SRS and SRN, and a control signal 117b to the first and second multiplexers 204a and 204b. Furthermore, the controller 108 supplies control signals 120s and 120n to the first and second sample-and-hold circuit units 203a and 203b, respectively. Moreover, the controller 108 supplies a control signal 129 to the first and second A/D converters 104a and 104b and a control signal 130 to the digital data processing circuit 105 so as to control the first and second A/D converters 104a and 104b and the digital data processing circuit 105. In addition, the controller 108 supplies a control signal 140 to the D/A converters DACa and DACb connected to the first and second differential amplifiers 205a and 205b so as to control direct current potentials to be added to analog electric signals output from the first and second differential amplifiers 205a and 205b.

Figure 2B:
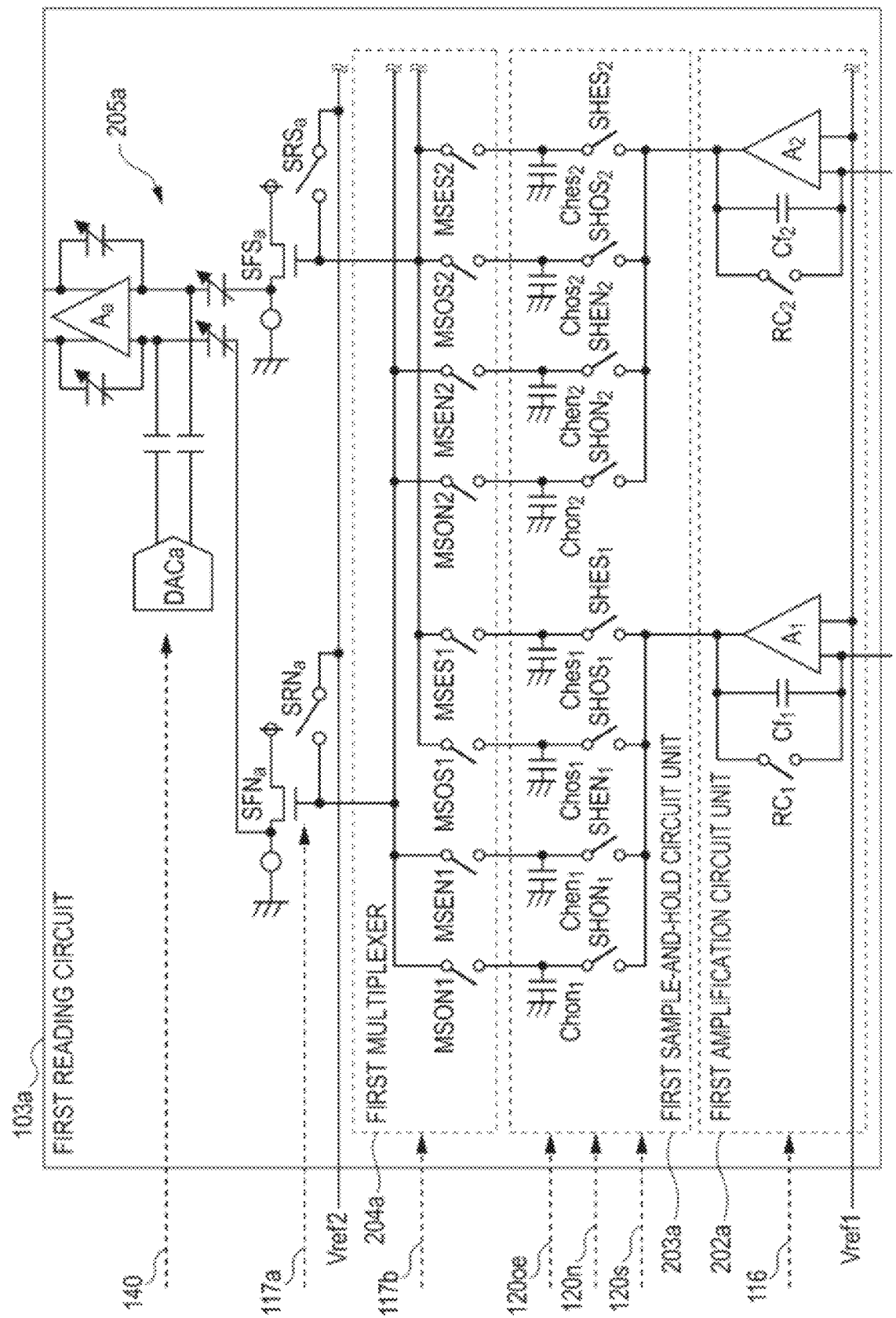
FIG. 2B is a diagram illustrating an equivalent circuit used to explain a reading circuit in detail.

FIG. 2B is a diagram illustrating an equivalent circuit used to explain the reading circuit unit 103 in detail. The first amplification circuit unit 202a includes amplifying circuits each of which includes a calculation amplifier A which amplifies and outputs electric signals (pixel signals) read from the pixels, an integrating capacitor Cf, a resetting switch RC which resets the integrating capacitor Cf. The calculation amplifier A has an inverting input terminal which receives an output electric signal and an output terminal which outputs an amplified electric signal. The calculation amplifier A has a non-inverting input terminal which receives the reference voltage Vref1 supplied from the power supply unit 107. Furthermore, the integrating capacitor Cf is disposed between the inverting input terminal and the output terminal of the calculation amplifier A, and the resetting switch RC is connected to the integrating capacitor Cf in parallel. The first sample-and-hold circuit unit 203a includes sample-and-hold circuits for odd-numbered row signals, sample-and-hold circuits for even-numbered row signals, sample-and-hold circuits for odd-numbered row noise, and sample-and-hold circuits for even-numbered row noise for individual amplifying circuits. Each of the sample-and-hold circuits for odd-numbered row signals includes a sampling switch SHOS which samples electric signals supplied from pixels in odd-numbered rows and a sampling capacitor Chos which holds pixel signals in the odd-numbered rows. Each of the sample-and-hold circuits for even-numbered row signals includes a sampling switch SHES which samples pixel signals in even-numbered rows and a sampling capacitor Ches which holds pixel signals in the even-numbered rows. Each of the sample-and-hold circuits for odd-numbered row noise includes a sampling switch SHON which samples a noise component of the calculation amplifier before the pixel signals of the odd-numbered rows are sampled and a sampling capacitor Chon which holds noise signals. Each of the sample-and-hold circuits for even-numbered row noise includes a sampling switch SHEN which samples noise of the calculation amplifier before the pixel signals of the even-numbered rows are sampled and a sampling capacitor Chen which holds noise signals. The first multiplexer 204a includes switches MSOS corresponding to the sample-and-hold circuits for odd-numbered row signals and switches MSES corresponding to the sample-and-hold circuits for even-numbered row signals for individual amplifying circuits. The first multiplexer 204a further includes switches MSON corresponding to the sample-and-hold circuits for odd-numbered row noise and switches MSEN corresponding to the sample-and-hold circuits for even-numbered row noise for individual amplifying circuits. Then, by successively selecting the switches, a process of converting the pixel signals or parallel signals of noise components into serial signals is performed.

Figure 3:
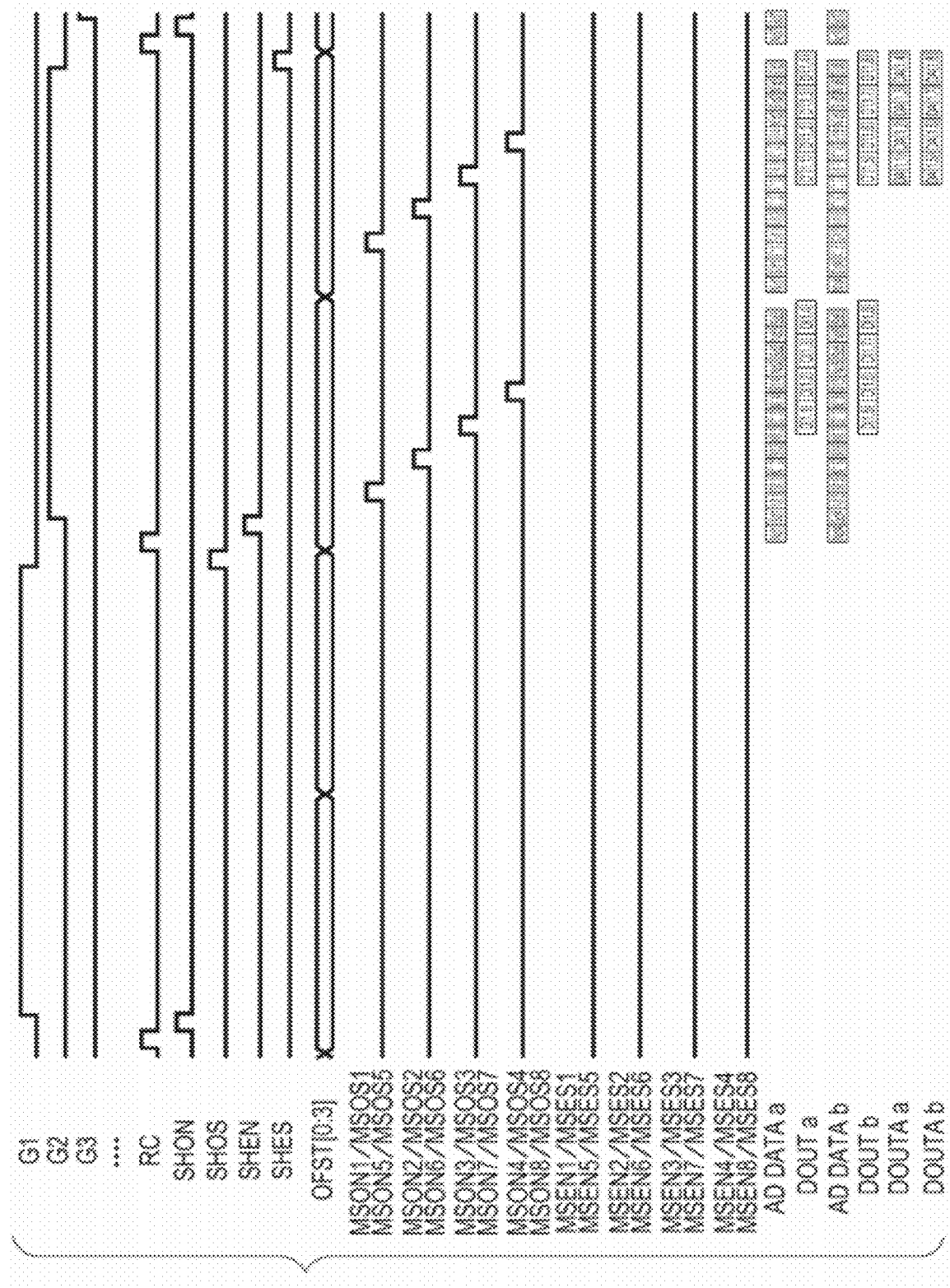
FIG. 3 is a timing chart illustrating operation of the image pickup apparatus according to the embodiment of the present invention.

Next, referring to FIGS. 2A, 2B, and 3, operation of the image pickup apparatus according to this embodiment of the present invention will be described. FIG. 3 is a timing chart illustrating an image pickup operation of the image pickup apparatus according to the embodiment of the present invention.

In the operation of this embodiment of the present invention, the following points should be kept in mind First, the image pickup apparatus according to this embodiment of the present invention performs an A/D conversion operation several times (twice in this embodiment) for an output operation performed on a row-by-row basis. That is, the image pickup apparatus performs the conversion operation several times for one signal. Next, the image pickup apparatus according to this embodiment of the present invention performs the A/D conversion operation several times by applying different direct current potentials to signals output from the reading circuit unit and input to the A/D converter. Then, the image pickup apparatus according to this embodiment of the present invention averages a plurality of digital data items obtained through the A/D conversion operation performed several times for one signal so as to supply single data.

First, the image pickup apparatus 100 performs an operation of outputting pixels on a row-by-row basis. Before the output operation is performed, the detector 101 is irradiated with a radial ray or a light beam and charges corresponding to the radial ray or the light beam are generated in the conversion elements S. When the output operation is started on a row-by-row basis, the controller 108 supplies the offset control signal 140 to the D/A converters DACa and DACb, and direct current potentials to be applied to signals output from the first and second differential amplifiers 205a and 205b which are analog electric signals output from the reading circuit unit 103 are set as first direct current potentials. Subsequently, the controller 108 supplies the control signal 116 to the resetting switches RC and the integrating capacitors Cf are reset by the resetting switches RC whereby the amplifying circuits are reset. Next, the controller 108 supplies control signals 120n and 12oe to the first and second sample-and-hold circuit units 203a and 203b. By this, the sampling switches SHON of the sample-and-hold circuits for odd-numbered row noise are brought to conductive states and noise components of the amplifying circuits which have been reset are transmitted to the sampling capacitors Chon. Then, the sampling switches SHON are brought to nonconductive states and the noise components are held in the sampling capacitors Chon. Next, the driving circuit 102 supplies the driving signals 111 to the driving line G1 of the first row so that the switch elements T11 to T18 of the first row are brought to conductive states. By this, analog electric signals which correspond to charges generated in the conversion elements S11 to S14 of the first row are transmitted from corresponding pixels to the first reading circuit 103a in parallel through the signal lines Sig1 to Sig4. Furthermore, the analog electric signals corresponding to charges generated in the conversion elements S15 to S18 of the first row are transmitted from corresponding pixels to the second reading circuit 103b in parallel through the signal lines Sig5 to Sig8. Then, the controller 108 supplies the control signals 120s and 120oe to the first and second sampleand-hold circuit units 203a and 203b. By this, the sampling switches SHOS of the sample-and-hold circuits for odd-numbered row signals are brought to conductive states, and read pixel signals are transmitted to the sampling capacitors Chos through the amplifying circuits. Here, noise components of the amplifying circuits are added to the pixel signals. Then, the sampling switches SHOS are brought to nonconductive states, and the pixel signals to which the noise components have been added are stored in the sampling capacitors Chon.

Next, the image pickup apparatus 100 performs a signal processing operation described below. The controller 108 supplies the control signal 117a to the reset switches SRS and SRN. By this, the reset switches SRS and SRN are brought to conductive states and the reference voltage Vref2 is applied to the gates of the buffers SRS and SRN whereby inputs of the first and second differential amplifiers 205a and 205b are reset. That is, the reset switches SRS and SRN serve as reset units which output reset signals to the first and second A/D converters 104a and 104b. Here, signals obtained by adding the first direct current potentials by the D/A converters DACa and DACb to the signals output from the first and second differential amplifiers 205a and 205b which have been reset are supplied to the first and second A/D converters 104a and 104b. That is, the first direct current potentials are added to the analog electric signals output from the reading circuit units by the D/A converters DACa and DACb and resultant signals are supplied to the first and second A/D converters 104a and 104b. Then, the first and second A/D converters 104a and 104b convert the input signals into digital data items Nd1 and Nd4 and supplies the digital data items Nd1 and Nd4 to the digital data processing circuit 105. The digital data items Nd1 and Nd4 are reset data items of the first and second differential amplifiers 205a and 205b including the first direct current potentials. Next, the reset switches SRS and SRN are brought to nonconductive states, meanwhile the signals to which the first direct current potentials have been added by the D/A converters DACa and DACb are supplied to the first and second A/D converters 104a and 104b. Then, the first and second A/D converters 104a and 104b convert the input signals into digital data items Sd1 and Sd4 and outputs the digital data items Sd1 and Sd4 to the digital data processing circuit 105. This operation is referred to as a pseudo data output operation.

Next, the reset switches SRS and SRN are brought to conductive states again, the reference voltage Vref2 is supplied to the gates of the buffers SFS and SFN, and the inputs of the first and second differential amplifiers 205a and 205b are reset again. At this time, the signals obtained by adding the first direct current potentials by the D/A converters DACa and DACb to the signals output from the first and second differential amplifiers 205a and 205b are input to the first and second A/D converters 104a and 104b. Then, the first and second A/D converters 104a and 104b convert the input signals into digital data items N(1, 1) and N(1, 5) and outputs the digital data items N(1, 1) and N(1, 5) to the digital data processing circuit 105. As with the digital data items Nd1 and Nd4, the digital data items N(1, 1) and N(1, 5) serve as reset data items for the first and second differential amplifiers 205a and 205b including the first direct current potentials. This operation is referred to as a reset data output operation.

Next, the controller 108 supplies the control signal 117b to the first and second multiplexers 204a and 204b. In response to the control signal 117b, switches MSOS1 and MSON1 of the first multiplexer 204a are brought to conductive states. By this, the pixel signals of the pixels in the first row to which noise components are added are supplied to the first differential amplifier 205a through the buffers SFS and the noise components are supplied to the first differential amplifier 205a through the buffers SFN. Furthermore, switches MSOS5 and MSON5 of the second multiplexer 204b are simultaneously brought to conductive states. By this, pixel signals of pixels in a fifth row to which noise components have been added are supplied to the second differential amplifier 205b through the buffers SFS and the noise components are supplied to the second differential amplifier 205b through the buffers SFN. The pixel signals to which the noise components are added and the noise components are subjected to a differential process by the first and second differential amplifiers 205a and 205b. Then, the pixel signals which have been subjected to the differential process are amplified and output from the first and second differential amplifiers 205a and 205b. By this, the noise components of the signals output from the amplifier circuits are removed. The first and second A/D converters 104a and 104b convert the output pixel signals into digital data items S(1, 1) and S(1, 5) and outputs the digital data items S(1, 1) and S(1, 5) to the digital data processing circuit 105. The digital data items S(1, 1) and S(1, 5) are obtained by adding the first direct current potentials to the pixel signals output from the first and second differential amplifiers 205a and 205b. The operation is referred to as a pixel data output operation.

Next, the reset data output operation is performed again, digital data items N(1, 2) and N(1, 6) are output from the first and second A/D converters 104a and 104b to the digital data processing circuit 105. The digital data items N(1, 2) and N(1, 6) are obtained by adding the first direct current potentials to the signals output from the first and second differential amplifiers 205a and 205b which have been reset.

Then, the pixel data output operation is performed on the second and sixth rows, and the first and second A/D converters 104a and 104b output the digital data items S(1, 2) and S(1, 6) to the digital data processing circuit 105. The digital data items S(1, 2) and S(1, 6) are obtained by adding the first direct current potentials to the pixel signals output from the first and second differential amplifiers 205a and 205b.

Similarly, the reset data output operation, the pixel data output operation for third and seventh rows, the reset data output operation, and the pixel data output operation for fourth and eighth rows are successively performed. By this, the digital data items N(1, 3) and N(1, 7), the digital data items S(1, 3) and S(1, 7), the digital data items N(1, 4) and N(1, 8), and the digital data items S(1, 4) and S(1, 8) are output. Here, the digital data items N(1, 3), N(1, 7), N(1, 4), and N(1, 8) are obtained by adding the first direct current potential to the signals output from the first and second differential amplifiers 205a and 205b which have been reset. Furthermore, the digital data items S(1, 3), S(1, 7), S(1, 4), and S(1, 8) are obtained by adding the first direct current potentials to the pixel signals output from the first and second differential amplifiers 205a and 205b.

Thereafter, the pseudo reset data output operation is performed twice, and the digital data items Nd2 and Nd5, the digital data items Sd2 and Sd5, the digital data items Nd3 and Nd6, and the digital data items Sd3 and Sd6 are output to the digital data processing circuit 105. These digital data items are, as with the pseudo reset data output operation described above, obtained by adding the first direct current potentials to the signals output from the first and second differential amplifiers 205a and 205b by the D/A converters DACa and DACb.

The data items output from the first and second A/D converters 104a and 104b are subjected to a correction process, which will be described hereinafter, by the digital data processing circuit 105 so that corrected pixel data items D(1, 1) to D(1, 4) and corrected pixel data items D(1, 5) to D(1, 8) are obtained.

As described above, the first signal processing operation is performed on the pixels on a row-by-row basis. The first signal processing operation includes the pseudo reset data output operation, the reset data output operation and the pixel data output operation performed on a row-by-row basis, and again the pseudo reset data output operation performed twice which use the first direct current potentials which have been added. The digital data items output from the A/D conversion unit 104 in the first signal processing operation are referred to as first digital data items.

Subsequently, the controller 108 supplies the offset control signal 140 to the D/A converters DACa and DACb, direct current potentials of signals output from the first and second differential amplifiers 205a and 205b are set as second direct current potentials, and a second signal processing operation similar to the first signal processing operation is performed on the pixels on a row-by-row basis. Specifically, the pseudo reset output operation is performed so that digital data items N'd1 and N'd4 are output. Then, the reset data output operation is performed on a row-by-row basis so that digital data items N'(1, 1), N'(1, 5), N'(1, 2), N'(1, 6), N'(1, 3), N'(1, 7), N'(1, 4), and N'(1, 8) are output. Furthermore, the pixel data output operation is performed so that digital data items S'(1, 1), S'(1, 5), S'(1, 2), S'(1, 6), S'(1, 3), S'(1, 7), S'(1, 4), and S'(1, 8) are output. Then, the pseudo reset data output operation is performed twice so that digital data items N'd2, N'd5, S'd2, S'd5, N'd3, N'd6, S'd3, and S'd6 are output. As with the first signal processing operation, the digital data processing circuit 105 performs the correction process, which will be described hereinafter, so that corrected pixel data items D'(1, 1) to D'(1, 4) and corrected pixel data items D'(1, 5) to D'(1, 8) are obtained. The digital data items output from the A/D conversion unit 104 in the second signal processing operation are referred to as second digital data items.

Then, the digital data processing circuit 105 averages the corrected pixel data items D(m, n) obtained through the first signal processing operation and the corrected pixel data items D'(m, n) obtained through the second signal processing operation for each data item corresponding to a pixel so as to generate output data items DA(m, n). This operation is referred to as an average processing operation. Then, a reading operation performed on pixels on a row-by-row basis is realized by the data processing operation including the first and second signal processing operations and the average processing operation. Then, the reading operation on a row-by-row basis is repeatedly performed so that a reading operation for one image is realized.

As described above, in this embodiment, while direct current potentials are changed for pixel signals of pixels included in the same row, the A/D conversion operation is performed twice and digital data items corresponding to the pixels are averaged so that final output data is obtained.

Here, in this embodiment, the pixel output operation for the second row is performed while the data processing operation for the first row is performed. First, as with the first row, the integrating capacitors Cf are reset by the reset switches Rc whereby the amplifying circuits are reset. Next, the sampling switches SHEN of the sample-and-hold circuits for even-numbered row noise are brought to conductive states, and noise components of the amplifying circuits which have been reset are transmitted to the sampling capacitors Chen. Then, the sampling switches SHEN are brought to nonconductive states and the noise components are stored in the sampling capacitors Chen. Next, the driving circuit 102 supplies the driving signals 111 to a driving line G2 of the second row so that switch elements T21 to T28 of the second row are brought to conductive states. By this, analog electric signals corresponding to charges generated in conversion switches S21 to S24 of the second row are transmitted to the first reading circuit 103a in parallel through the signal lines Sig1 to Sig4 from pixels. Furthermore, analog electric signals corresponding to charges generated in conversion elements S25 to S28 of the second row are transmitted to the second reading circuit 103b in parallel through the signal lines Sig5 to Sig8 from pixels. Then, the sampling switches SHES of the sample-and-hold circuits for even-numbered row signals are brought to conductive states, and read pixel signals are transmitted to sampling capacitors Ches through the amplifying circuits. Here, the noise components of the amplifying circuits are added to the pixel signals. Then, the sampling switches SHES are brought to nonconductive states and the pixel signals to which the noise components are added are stored in the sampling capacitors Chen. In the pixel data output operation for the second row, as with the first row, the switches MSES and MSEN of the first and second multiplexers 204a and 204b are successively brought to conductive states. Other operations are the same as those performed on the first row. In order to perform the output operation and the data processing operation, the output operation for a certain row is performed while the output operation for a preceding row is performed. Therefore, when compared with a case where the output operation for the certain row is performed after the output operation for the preceding row is performed, a period of time required for the reading operation for one image can be reduced.

Figure 4A:
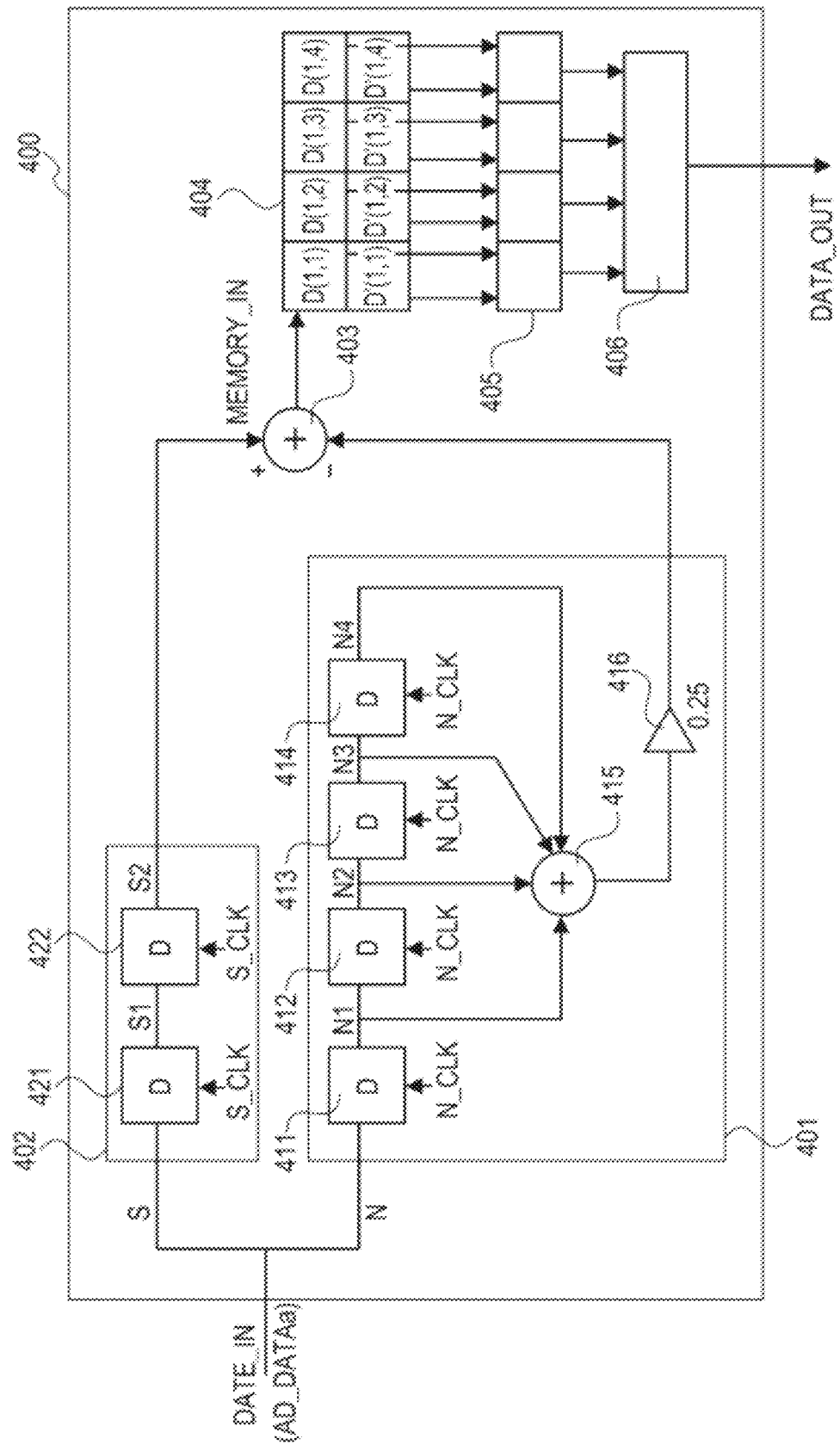
FIG. 4A is a block diagram illustrating operation of a signal processing unit according to the embodiment of the present invention.
Figure 4B:
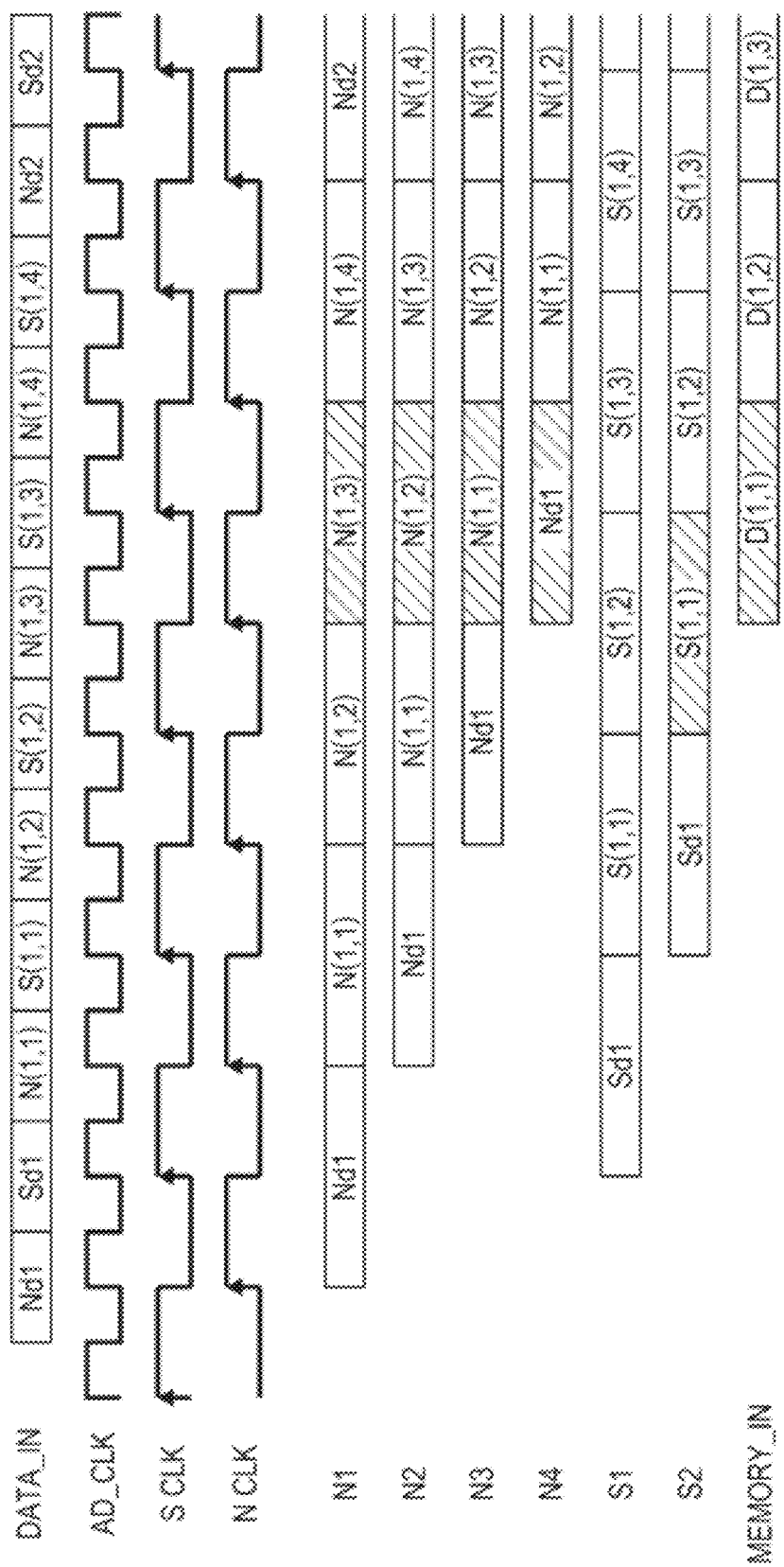
FIG. 4B is a timing chart illustrating a correction process performed by a correction processor.

Next, the correction process performed by the digital data processing circuit 105 will be described with reference to FIGS. 4A and 4B. FIG. 4A is a block diagram illustrating a correction processor 400 included in the digital data processing circuit 105. FIG. 4B is a timing chart illustrating the correction process performed by a reset data processor 401, a pixel data processor 402, and an adder 403. Note that, in this embodiment, the correction processor 400 shown in FIG. 4A is provided for each of the first and second A/D converters 104a and 104b. In the following description, the correction processor 400 is provided for the first A/D converter 104a. Note that the correction processor is not limited to this and may be provided for performing a correction process on data items which have been supplied from the first and second A/D converters 104a and 104b and which have been subjected to digital multiplexing.

The correction processor 400 includes the reset data processor 401, the pixel data processor 402, the adder 403, a storage unit 404, an average processor 405, and a parallel/serial converter 406. Here, the reset data processor 401 includes a plurality of delay elements 411 to 414, an adder 415, and a multiplier 416. The pixel data processor 402 includes a plurality of delay elements 421 and 422.

In accordance with the control signal 130 supplied from the controller 108, a clock signal N_CLK is supplied to the delay elements 411 to 414 of the reset data processor 401 and a clock signal S_CLK is supplied to the delay elements 421 and 422 of the pixel data processor 402. The digital data item Nd1 output from the first A/D converter 104a in response to the first signal processing operation is supplied to the correction processor 400 and stored in the delay element 411 of the reset data processor 401 in response to a rising edge of the clock signal N_CLK. Next, the digital data item Sd1 is supplied to the correction processor 400 and stored in the delay element 421 of the pixel data processor 402 in response to a rising edge of the clock signal S_CLK. Next, the data item N(1, 1) is supplied to the correction processor 400 and is stored in the delay element 411 in response to a rising edge of the clock signal N_CLK, and the data item Nd1 is stored in the delay element 412. Next, the data item S(1, 1) is supplied to the correction processor 400 and is stored in the delay element 421 in response to a rising edge of the clock signal S_CLK. Next, the data item N(1, 2) is supplied to the correction processor 400 and is stored in the delay element 411 in response to a rising edge of the clock signal N_CLK, the data item N(1, 1) is stored in the delay element 412, and the data item Nd1 is stored in the delay element 413. Next, the data item S(1, 2) is supplied to the correction processor 400 and is stored in the delay element 421 in response to a rising edge of the clock signal S_CLK. The data item S(1, 1) is stored in the delay element 422 and is output from the delay element 422 to the adder 403. Then, the data item N(1, 3) is supplied to the correction processor 400 and is stored in the delay element 411 in response to a rising edge of the clock signal N_CLK. The data item N(1, 2) is stored in the delay element 412, the data item N(1, 1) is stored in the delay element 413, and the data item Nd1 is stored in the delay element 414. Then, signals output from the delay elements 411 to 414 are supplied to the adder 415 so as to be added to one another. A resultant signal is reduced to a quarter thereof for averaging by the multiplier 416 and is supplied to the adder 403. The adder 403 performs a subtraction process using the data output from the pixel data processor 402 and the data output from the reset data processor 401 and outputs corrected pixel data D(1, 1). Through this process, the pixel data D(1, 1) is obtained by the following expression: S(1, 1)−(Nd1+N(1, 1)+N(1, 2)+N(1, 3))/4. Similarly, the pixel data D(1, 2) is obtained by the following expression: S(1, 2)−(N(1, 1)+N(1, 2)+N(1, 3)+N(1, 4))/4. Specifically, in the correction process, first, the reading circuit 103 supplies a plurality of reset signals to the A/D converters while the signal processing operation is performed on a row-by-row basis. The first and second A/D converters 104a and 104b convert the reset signals into reset data items. The correction processor 400 performs an addition average process on the reset data items output from the first and second A/D converters 104a and 104b. Then, the correction processor 400 performs a subtraction process using the pixel data items which have been output from the first and second A/D converters 104a and 104b in the same period and the reset data items which have been subjected to the addition average process so that pixel data items D(m, n) are obtained. Furthermore, in this embodiment, for pixel data to be subjected to the correction process, four reset data items which include preceding two reset data items and succeeding two reset data items and which are successively output in terms of time are subjected to the addition average process. By this, reset data items including high-frequency noise components and reset data items including low-frequency 1/f noise components are subjected to the addition average process whereby the high-frequency noise components included in the processed reset data items are suppressed. That is, in the addition average process, the reset data items undergo a low-pass filter (LPF). Therefore, the reset data items which have been subjected to the addition average process mainly include the low-frequency 1/f noise components. Accuracy of the LPF process is improved by increasing the number of reset data items to be subjected to the addition average process. Then, subtraction is performed using the pixel data items including the low-frequency 1/f noise components and the reset data items which have been subjected to the addition average process whereby the 1/f noise components are appropriately reduced from the pixel data items. In the subtraction process, the pixel data items undergo a high-pass filter (HPF). That is, in the correction process, the LPF process and the HPF process are performed on the pixel data items, and therefore, the correction process is appropriately performed. Note that reset data items to be subjected to the addition average process are not limited to preceding two reset data items and succeeding two reset data items as long as the number of preceding reset data items and the number of succeeding reset data items are the same as each other. The pixel data items D(1, 1) to D(1, 4) output from the adder 403 are stored in the storage unit 404. The process described above are similarly performed in the second signal processing operation, and the pixel data items D'(1, 1) to D'(1, 4) are also stored in the storage unit 404.

Next, the average processor 405 performs an averaging process using the pixel data items D(1, 1) and D'(1, 1) in the first row and the first column as a pair so as to output a corrected pixel data item DA(1, 1). Similarly, the average processor 405 performs the averaging process on a pair of the pixel data items D(1, 2) and D'(1, 2), a pair of pixel data items D(1, 3) and D'(1, 3), and a pair of pixel data items D(1, 4) and D'(1, 4). The pixel data items which have been subjected to the averaging process are converted into serial data items by a parallel/serial converter 406 so that corrected pixel data items DA(1, 1), DA(1, 2), DA(1, 3), and DA(1, 4) are successively output.

Next, information on nonlinearities of the A/D converters will be described. Nonlinearity represents a difference between an ideal line and the relationship between an actual analog input and a digital output (A/D conversion value). Specifically, the nonlinearity is represented by a differential nonlinearity (DNL) or an integral nonlinearity (INL). The INL means a difference between an ideal input/output line and an actual input/output characteristic in an entire input/output characteristic of an A/D converter. The DNL means a difference between ideal steps and input and output steps.

Figure 5A:
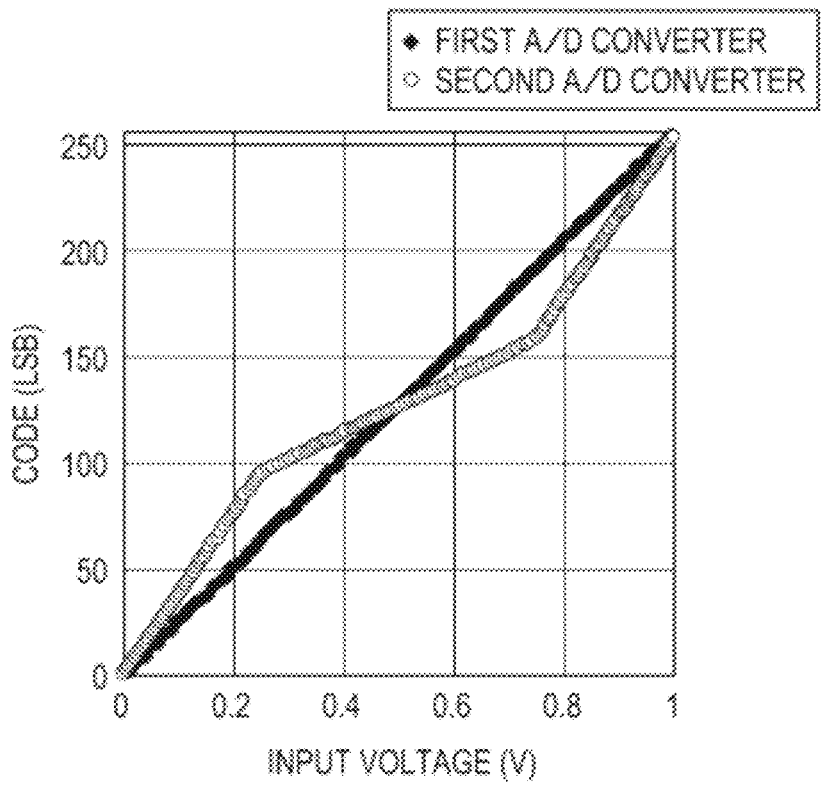
FIG. 5A is a diagram illustrating an adverse effect caused by a difference among A/D conversion characteristics of A/D converters.

Hereinafter, adverse effects caused by a difference between A/D conversion characteristics of the first and second A/D converters 104a and 104b will be described with reference to FIGS. 5A and 5B. FIG. 5A illustrates nonlinearities of the first and second A/D converters 104a and 104b. Here, the first A/D converter 104a has an ideal A/D conversion characteristic whereas the second A/D converter 104b has a nonlinearity shifted from the ideal characteristic. In FIG. 5A, an axis of abscissa denotes an input voltage to be input to the first and second A/D converters 104a and 104b and an axis of ordinate denotes a digital value (code) output from the first and second A/D converters 104a and 104b. Note that, in FIG. 5A, for simplicity of the description, the first and second A/D converters 104a and 104b have a resolution capability of 8 bits.

Figure 5B:
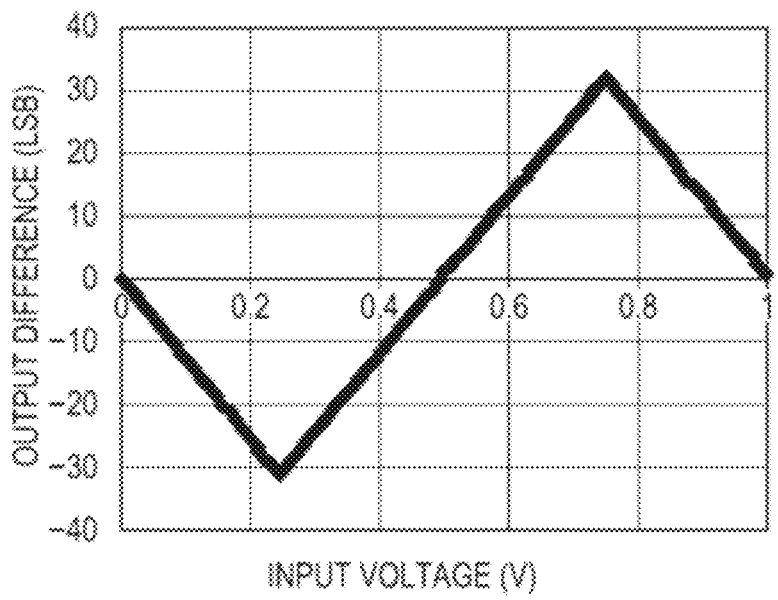
FIG. 5B is a diagram illustrating an adverse effect caused by a difference among A/D conversion characteristics of A/D converters.

FIG. 5B illustrates a difference between digital values corresponding to input voltages of the first and second A/D converters 104a and 104b. According to FIG. 5B, when the input voltages of the first and second A/D converters 104a and 104b are converted into digital values without change and are output, an output difference of 30 LSB at a maximum between the first and second A/D converters 104a and 104b is generated. Therefore, an image tone unevenness of approximately 30 LSB at a maximum may be generated between the first and second pixel groups 101a and 101b corresponding to the first and second A/D converters 104a and 104b, respectively. In particular, as described in this embodiment, when the first and second pixel groups 101a and 101b are obtained by dividing an entire region of the detector 101, the tone unevenness is remarkably viewed at a boundary between the first and second pixel groups 101a and 101b. Consequently, quality of an obtained image is considerably deteriorated.

Therefore, in this embodiment of the present invention, a process of adding direct current potentials to analog electric signals to be input to the first and second A/D converters 104a and 104b by adding direct current potentials to signals output from the first and second differential amplifiers 205a and 205b connected to the first and second A/D converters 104a and 104b by the controller 108 is performed. For example, it is assumed that a direct current potential of 300 mV is set in the first signal processing operation, and signals corresponding to 400 mV are input to the first and second A/D converters 104a and 104b. In this case, an unevenness of approximately −15 LSB is generated between the first and second pixel groups 101a and 101b due to a difference between the nonlinearities of the first and second A/D converters 104a and 104b. Next, it is assumed that a direct current potential of 500 mV is set in the second signal processing operation and signals corresponding to 600 mV are input to the first and second A/D converters 104a and 104b. In this case, an unevenness of approximately +15 LSB is generated between the first and second pixel groups 101a and 101b due to the difference between the nonlinearities of the first and second A/D converters 104a and 104b. Then, results of the first and second signal processing operations are averaged, and the unevenness can be reduced. Note that, when characteristics of the first and second A/D converters 104a and 104b have been known, the reduction of the unevenness can be effectively attained by appropriately selecting the direct current potentials to be added. Therefore, the controller 108 preferably perform the foregoing process in accordance with information on the nonlinearities of the first and second A/D converters 104a and 104b stored in another storage unit, for example. The process of reducing a difference between an average value of the digital signals output from the first A/D converter 104a and an average value of the digital signals output from the second A/D converter 104b can be performed in accordance with the information. By this, a process of reducing tone unevenness can be performed with higher accuracy. However, the embodiment of the present invention is applicable even when the characteristics of the first and second A/D converters 104a and 104b are unknown, and the effect of the reduction of the unevenness can be obtained. When the characteristics of the first and second A/D converters 104a and 104b are unknown, the signal processing operation is more preferably performed as many as possible, that is, at least four times for each row with different direct current potentials. In particular, when the signal processing operation is performed four times or more, quantization errors of the A/D converters are reduced to half or less, that is, a special effect other than the reduction of the difference between the nonlinearities is generated. Furthermore, the embodiment of the present invention is suitably applicable to an image pickup apparatus which employs pipeline A/D converters which is likely to generate nonlinearity errors in terms of structure.

Note that when the process described above is performed only on image signals at a time of shooting, undesired signal components are added to the image signals to be obtained, and therefore, reliability of the obtained image signals is degraded. Accordingly, in this embodiment of the present invention, correction image signals used to correct the image signals at a time of shooting such as image signals used for offset correction for correcting output signals under a dark condition and image signals used for sensitivity correction and image signals at a time of shooting are obtained through a similar process. Then, the digital data processing circuit 105 performs the correction process using obtained image data for correction and image data obtained at a time of shooting so as to output corrected image data. By performing this process, the undesired signal components which have been added are removed or reduced, a feeling of strangeness caused by unevenness or the like is reduced, and an image having an excellent quality can be obtained.

Note that, in this embodiment, an amount of change between direct current potentials output from the first and second differential amplifiers 205a and 205b in the first signal processing operation and direct current potentials output from the first and second differential amplifiers 205a and 205b in the second signal processing operation may be obtained in real time through calculation performed by the controller 108 on the basis of the information stored in the storage unit (not shown). Furthermore, the amount of change may be determined in advance on the basis of information on the nonlinearities of the first and second A/D converters 104a and 104b.

Furthermore, in this embodiment, the case where the two A/D converters are employed is described. However, three or more A/D converters may be employed. The process described above is preferably performed on all the A/D converters. However, the process may be performed on only some of the A/D converters.

Furthermore, as a method for adding the direct current potentials to the signals input to the first and second A/D converters 104a and 104b, D/A converters DACa and DACb which are connected through the capacitors to input sides of the first and second differential amplifiers 205a and 205b are used. This configuration is desirable to address the problem. However, the present invention is not limited to this. Furthermore, although the direct current potentials of the analog signals to be input to the first and second A/D converters 104a and 104b are changed in this embodiment, even when gains are changed using units having variable capacitors as the differential amplifiers, the same effect can be obtained. Moreover, although the averaging process is performed using the pixel data items D(m, n) which have been subjected to the addition average process and the subtraction process in this embodiment, the embodiment of the present invention is not limited to this. The effects of the invention is attained only by performing the averaging process on the pixel data items S(m, n) and S'(m, n). Thereafter, the addition average process and the subtraction process may be performed.

Figure 6A:
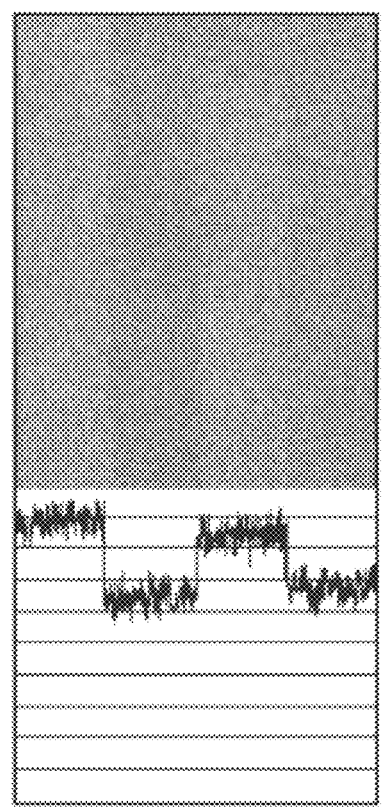
FIG. 6A is a diagram illustrating image data which has not been subjected to the correction process.
Figure 6B:
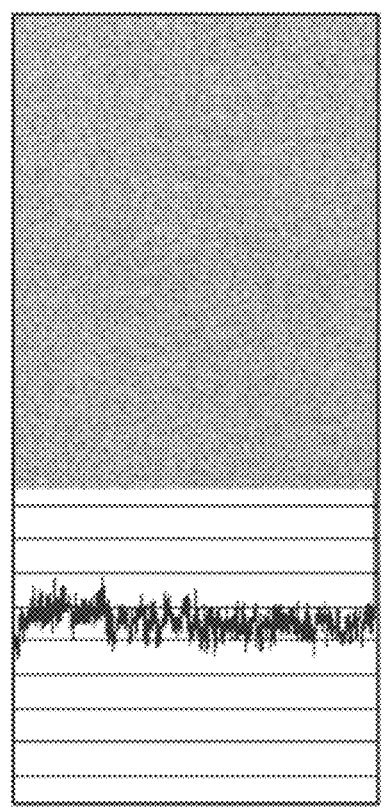
FIG. 6B is a diagram illustrating image data which has been subjected to the correction process.

Referring to FIGS. 6A and 6B, the effect of the embodiment of the present invention will be described. FIG. 6A illustrates image data which has not been subjected to the correction process whereas FIG. 6B illustrates image data which has been subjected to the correction process. Here, a case where the detector 101 is divided into four pixel groups is shown as an example. The image data which has been subjected to the correction process attains a better image since unevenness among the pixel groups is undistinguished when compared with the image data which has not been subjected to the correction process. By reducing the unevenness among the pixel groups as described above, artifacts of an obtained image can be reduced. Accordingly, the correction processor 400 which performs the correction process can reduce the artifacts of the obtained image caused by the unevenness generated due to differences among nonlinearities (INLs) of the A/D converters.

Figure 7:
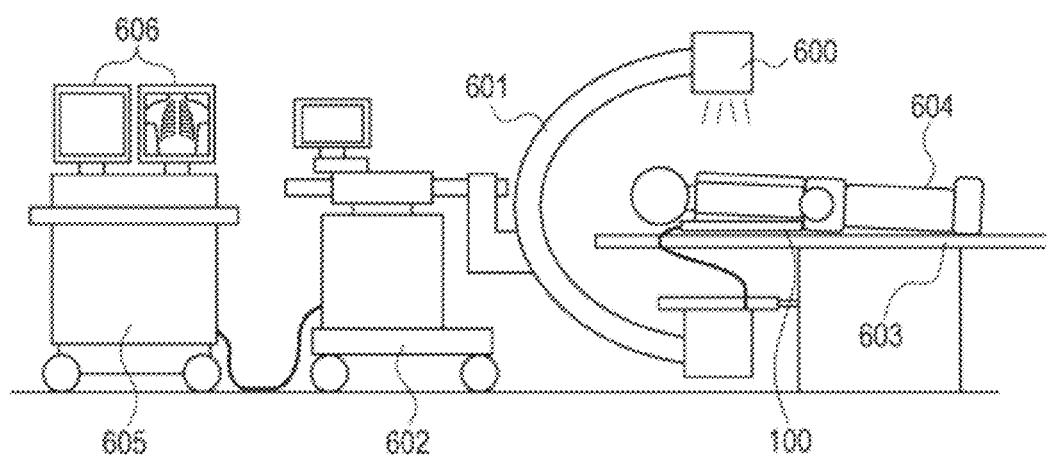
FIG. 7 is a diagram schematically illustrating a radiation image pickup system employing the image pickup apparatus according to the embodiment of the present invention.

Next, an application example of the image pickup apparatus according to the embodiment of the present invention employed in a movable radiation image pickup system will be described with reference to FIG. 7. FIG. 7 is a diagram schematically illustrating a movable image pickup system employing an image pickup apparatus capable of capturing moving images and still images. In FIG. 7, a reference numeral 600 denotes a radial-ray generation apparatus, and a reference numeral 601 denotes a C-shaped arm which functions as a support unit which supports the image pickup apparatus 100. A reference numeral 602 denotes a dolly used to move the radial-ray generating apparatus 600, the image pickup apparatus 100, and the C-shaped arm 601. Furthermore, a reference numeral 603 denotes a bed on which a test body 604 is mounted, a reference numeral 605 denotes a movable controller which controls the devices described above, and a reference numeral 606 denotes a display apparatus capable of displaying image signals obtained by the image pickup apparatus 100. The controller 605 includes a control computer, a control console, a radiation control device, and the like, and is capable of transmitting the image signals obtained by the image pickup apparatus 100 to the display apparatus 606 or the like after performing an image process on the image signals. By this, a doctor in a distant place can make a diagnosis using an image corresponding to the transmitted image data. Furthermore, the transmitted image data may be recorded in a film and stored in a storage unit such as an optical disc.

Note that the image pickup apparatus 100 may be detachable from the C-shaped arm 601 and a radial-ray generation apparatus which is different from the radial-ray generation apparatus 600 including the C-shaped arm 601 may be used for shooting.

As described above, since the image pickup apparatus according to the embodiment of the present invention is employed in the radiation image pickup system, a desired frame time is attained while image signals having an excellent S/N ratio can be obtained.

Note that, in this embodiment of the present invention, the processing steps performed by the controller 108 may be realized by executing programs by a computer included in the controller 108. In this case, a lookup table LUT and the programs are stored in the controller 108. Furthermore, a unit used to supply the programs to the computer including a computer readable recording medium such as a CD-ROM which stores the programs therein or a transmission medium such as the Internet which transmits the programs may be employed as an embodiment of the present invention. Furthermore, computer program products including the computer readable recording medium which stores the programs therein are employed as an embodiment of the present invention. The programs, the recording medium, the transmission medium, and the computer program products are included in the scope of the invention. Examples of the recording medium include a flexible disk, a hard disk, an optical disc, a magneto-optical disc, a CD-ROM, an electromagnetic tape, a nonvolatile memory card, and a ROM.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-245805, filed Oct. 26, 2009, which is hereby incorporated by reference herein in its entirety.

REFERENCE SIGNS LIST

100 Image pickup apparatus
101 Detector
102 Driving circuit
103 Reading circuit unit
104 A/D converter unit
105 Digital data processing circuit
106 Signal processor
107 Power supply unit
108 Controller

The invention claimed is:

1. An image pickup apparatus comprising:
a detector configured to include a plurality of pixels which are arranged in a matrix, which are used to convert a radial-ray or a light beam into analog electric signals, and which are divided into at least first and second pixel groups;
a signal processor configured to include a reading circuit unit which includes a first reading circuit electrically connected to the first pixel group and a second reading circuit electrically connected to the second pixel group and which reads the analog electric signals output from the detector on a row-by-row basis, an analog-to-digital (A/D) conversion unit which includes a first A/D converter electrically connected to the first reading circuit and a second A/D converter electrically connected to the second reading circuit and which converts the analog electric signals output from the reading circuit unit into digital data items and outputs the digital data items, and a digital data processing circuit which processes the digital data items;
a storage unit configured to store information on nonlinearities of the first and second A/D converters; and
a controller configured to control the signal processor,
wherein the signal processor further includes a direct current potential control circuit which changes the direct current potentials in accordance with a control signal supplied from the controller, and
wherein the controller controls the signal processor so that the signal processor performs a signal processing operation several times of adding direct current potentials to analog electric signals of certain pixels output from the reading circuit unit, supplying the resultant signals to the A/D conversion unit, and outputting digital data items to the digital data processing circuit while the direct current potentials are changed in accordance with the information stored in the storage unit, and an average processing operation of averaging the output digital data items corresponding to the certain pixels using the digital data processing circuit.

2. The image pickup apparatus according to claim 1, wherein
the direct current potential control circuit changes the direct current potentials into four or more different direct current potentials in accordance with the control signal supplied from the controller, and
the signal processor performs the signal processing operation with the four or more different direct current potentials.

3. The image pickup apparatus according to claim 1, wherein the direct current potential control circuit includes D/A converters and capacitors.

4. The image pickup apparatus according to claim 1, wherein pipeline A/D converters are employed as the first and second A/D converters.

5. An image pickup system comprising:
an image pickup apparatus according to claim 1; and
a control apparatus configured to control at least the image pickup apparatus.

6. A method for controlling an image pickup apparatus including a detector configured to include a plurality of pixels which are arranged in a matrix, which are used to convert a radial-ray or a light beam into analog electric signals, and which are divided into at least first and second pixel groups, and a signal processor configured to include a reading circuit unit which includes a first reading circuit electrically connected to the first pixel group and a second reading circuit electrically connected to the second pixel group and which reads the analog electric signals output from the detector on a row-by-row basis, an A/D conversion unit which includes a first A/D converter electrically connected to the first reading circuit and a second A/D converter electrically connected to the second reading circuit and which converts the analog electric signals output from the reading circuit unit into digital data items and outputs the digital data items, a digital data processing circuit which processes the digital data items, and a storage unit configured to store information on nonlinearities of the first and second A/D converters, the method comprising:

a signal processing operation of adding direct current potentials to analog electric signals of certain pixels output from the reading circuit unit, supplying the resultant signals to the A/D conversion unit, and outputting digital data items to the digital data processing circuit while the direct current potentials are changed in accordance with the information stored in the storage unit which is performed several times; and an average processing operation of averaging the output digital data items corresponding to the certain pixels using the digital data processing circuit.

7. An image pickup apparatus comprising:

a detector configured to include a plurality of pixels which are arranged in a matrix, which are used to convert a radial-ray or a light beam into analog electric signals, and which are divided into at least first and second pixel groups;

a signal processor configured to include a reading circuit unit which includes a first reading circuit electrically connected to the first pixel group and a second reading circuit electrically connected to the second pixel group and which reads the analog electric signals output from the detector on a row-by-row basis, an A/D conversion unit which includes a first A/D converter electrically connected to the first reading circuit and a second A/D converter electrically connected to the second reading circuit and which converts the analog electric signals output from the reading circuit unit into digital data items and outputs the digital data items, and a digital data processing circuit which processes the digital data items;

a storage unit configured to store information on nonlinearities of the first and second A/D converters; and a controller configured to control the signal processor, wherein the signal processor further includes a direct current potential control circuit which changes the direct current potentials in accordance with a control signal supplied from the controller, and wherein the controller controls the signal processor so that the signal processor performs a first signal processing operation of adding first direct current potentials to analog electric signals of certain pixels output from the reading circuit unit, supplying the resultant signals to the A/D conversion unit, and outputting first digital data items to the digital data processing circuit, a second signal processing operation of adding second direct current potentials which are changed from the first direct current potentials in accordance with the information stored in the storage unit to analog electric signals of certain pixels, supplying the resultant signals to the A/D conversion unit, and outputting second digital data items to the digital data processing circuit, and an average processing operation of averaging the first digital data items and the second digital data items using the digital data processing circuit.

8. An image pickup apparatus comprising:

a detector configured to include a plurality of pixels which are arranged in a matrix, which are used to convert a radial-ray or a light beam into analog electric signals, and which are divided into at least first and second pixel groups;

a signal processor configured to include a reading circuit unit which includes a first reading circuit electrically connected to the first pixel group and a second reading circuit electrically connected to the second pixel group and which reads the analog electric signals output from the detector on a row-by-row basis, an analog-to-digital (A/D) conversion unit which includes a first A/D converter electrically connected to the first reading circuit and a second A/D converter electrically connected to the second reading circuit and which converts the analog electric signals output from the reading circuit unit into digital data items and outputs the digital data items, and a digital data processing circuit which processes the digital data items; and a controller configured to control the signal processor, wherein the signal processor further includes a direct current potential control circuit which changes the direct current potentials in accordance with a control signal supplied from the controller, and wherein the controller controls the signal processor so that the signal processor performs a signal processing operation several times of adding direct current potentials to analog electric signals of certain pixels output from the reading circuit unit, supplying the resultant signals to the A/D conversion unit, and outputting digital data items to the digital data processing circuit while the direct current potentials are changed in accordance with a predetermined amount of change, and an average processing operation of averaging the output digital data items corresponding to the certain pixels using the digital data processing circuit.

9. The image pickup apparatus according to claim 8, wherein the direct current potential control circuit changes the direct current potentials into four or more different direct current potentials in accordance with the control signal supplied from the controller, and the signal processor performs the signal processing operation with the four or more different direct current potentials.

10. The image pickup apparatus according to claim 8, wherein the direct current potential control circuit includes digital-to-analog (D/A) converters and capacitors.

11. The image pickup apparatus according to claim 8, wherein pipeline A/D converters are employed as the first and second A/D converters.

12. An image pickup system comprising:

an image pickup apparatus according to claim 8; and a control apparatus configured to control at least the image pickup apparatus.

13. A method for controlling an image pickup apparatus including a detector configured to include a plurality of pixels which are arranged in a matrix, which are used to convert a radial-ray or a light beam into analog electric signals, and which are divided into at least first and second pixel groups, and a signal processor configured to include a reading circuit unit which includes a first reading circuit electrically connected to the first pixel group and a second reading circuit electrically connected to the second pixel group and which reads the analog electric signals output from the detector on a row-by-row basis, an A/D conversion unit which includes a first A/D converter electrically connected to the first reading circuit and a second A/D converter electrically connected to the second reading circuit and which converts the analog electric signals output from the reading circuit unit into digital data items and outputs the digital data items, and a digital data processing circuit which processes the digital data items, the method comprising:

- a signal processing operation of adding direct current potentials to analog electric signals of certain pixels output from the reading circuit unit, supplying the resultant signals to the A/D conversion unit, and outputting digital data items to the digital data processing circuit while the direct current potentials are changed in accordance with a predetermined amount of change which is performed several times; and
- an average processing operation of averaging the output digital data items corresponding to the certain pixels using the digital data processing circuit.

14. An image pickup apparatus comprising:

a detector configured to include a plurality of pixels which are arranged in a matrix, which are used to convert a radial-ray or a light beam into analog electric signals, and which are divided into at least first and second pixel groups;

a signal processor configured to include a reading circuit unit which includes a first reading circuit electrically connected to the first pixel group and a second reading circuit electrically connected to the second pixel group and which reads the analog electric signals output from the detector on a row-by-row basis, an analog-to-digital (A/D) conversion unit which includes a first A/D converter electrically connected to the first reading circuit and a second A/D converter electrically connected to the second reading circuit and which converts the analog electric signals output from the reading circuit unit into digital data items and outputs the digital data items, and a digital data processing circuit which processes the digital data items; and a controller configured to control the signal processor, wherein the signal processor further includes a direct current potential control circuit which changes the direct current potentials in accordance with a control signal supplied from the controller, and wherein the controller controls the signal processor so that the signal processor performs a first signal processing operation of adding first direct current potentials to analog electric signals of certain pixels output from the reading circuit unit, supplying the resultant signals to the A/D conversion unit, and outputting first digital data items to the digital data processing circuit, a second signal processing operation of adding second direct current potentials which are changed from the first direct current potentials in accordance with a predetermined amount of change to analog electric signals of certain pixels, supplying the resultant signals to the A/D conversion unit, and outputting second digital data items to the digital data processing circuit, and an average processing operation of averaging the first digital data items and the second digital data items using the digital data processing circuit.

* * * * *

UNITED STATES PATENT AND TRADEMARK OFFICE
CERTIFICATE OF CORRECTION

| | | |
|---|---|---|
| PATENT NO. | : 8,907,294 B2 | |
| APPLICATION NO. | : 13/502509 | |
| DATED | : December 9, 2014 | |
| INVENTOR(S) | : Kameshima et al. | |

It is certified that error appears in the above-identified patent and that said Letters Patent is hereby corrected as shown below:

On the Title page, Item (22), after the phrase "PCT Filed:"

Delete "Jun. 10, 2010" and insert instead -- Oct. 6, 2010 --.

Signed and Sealed this
Sixth Day of October, 2015

Michelle K. Lee
*Director of the United States Patent and Trademark Office*